United States Patent [19]

Borschneck

[11] Patent Number: 4,463,750
[45] Date of Patent: Aug. 7, 1984

[54] TRACTION DEVICE

[76] Inventor: Anthony G. Borschneck, 15603 Prospect Dr., Redding, Calif. 96001

[21] Appl. No.: 461,085

[22] Filed: Jan. 26, 1983

[51] Int. Cl.³ ............................................. A61H 1/02
[52] U.S. Cl. .................................... 128/75; 128/84 C
[58] Field of Search ..................... 128/75, 84 R, 84 C, 128/133, 134, 85

[56] References Cited

U.S. PATENT DOCUMENTS

| 3,596,655 | 8/1971 | Corcoran | 128/84 R |
| 3,732,863 | 5/1973 | Harrington | 128/75 |
| 4,252,113 | 2/1981 | Scire | 128/134 |
| 4,267,830 | 5/1981 | Vick | 128/134 |
| 4,400,820 | 8/1983 | O'Dell et al. | 128/134 |

Primary Examiner—John D. Yasko
Attorney, Agent, or Firm—Lothrop & West

[57] ABSTRACT

A supine patient with a spinal dislocation or fracture is supported for transportation by a base board having a harness to confine the patient's torso and head and having cups slidable along the base board and engageable with opposite sides of the patient's skull. The cups are not only movable longitudinally of the base board by a manually operable cable acting against a spring, but are also simultaneously urged toward the base board. The cups are likewise movable toward and away from each other transversely into latched positions.

10 Claims, 9 Drawing Figures

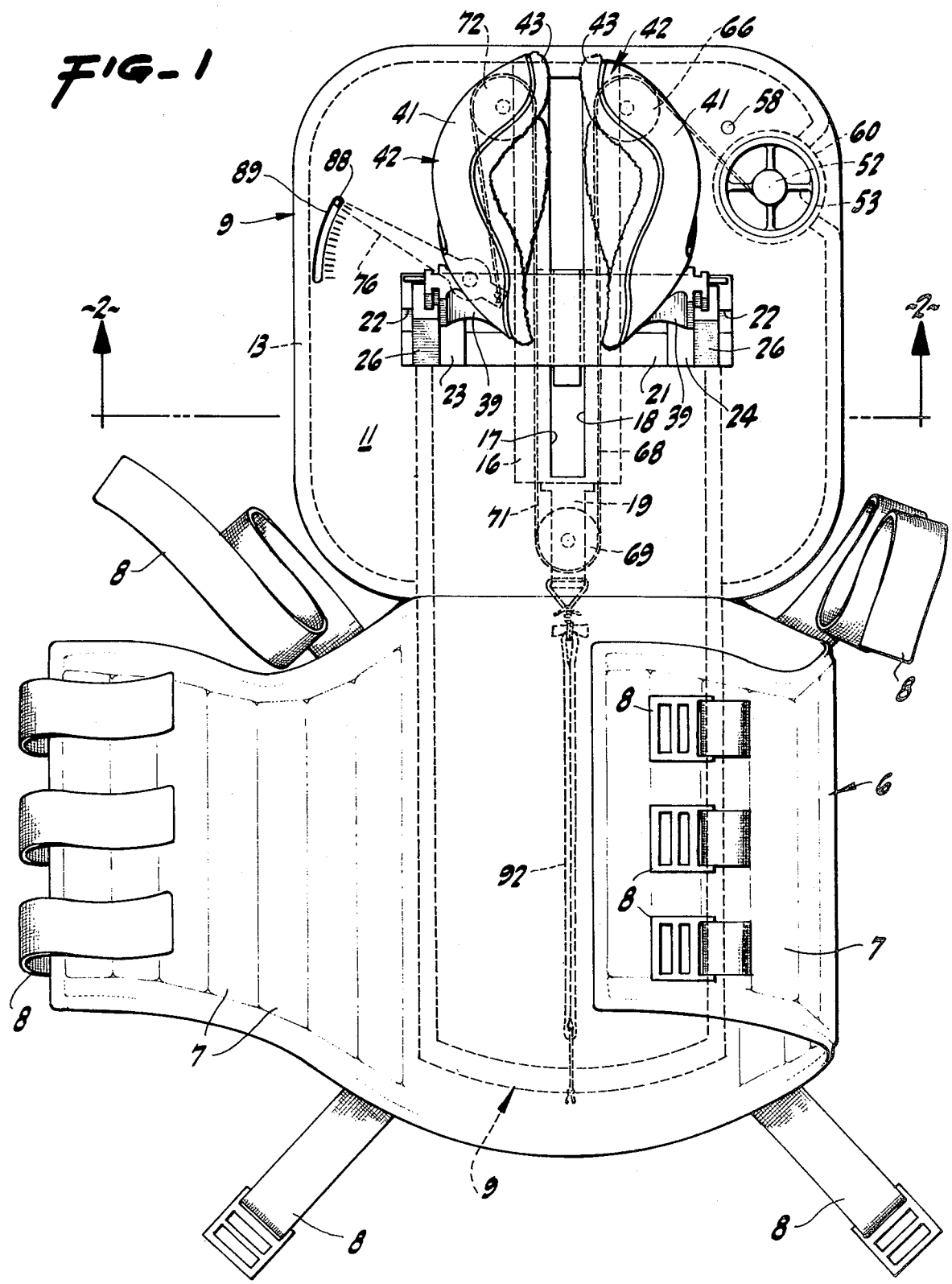

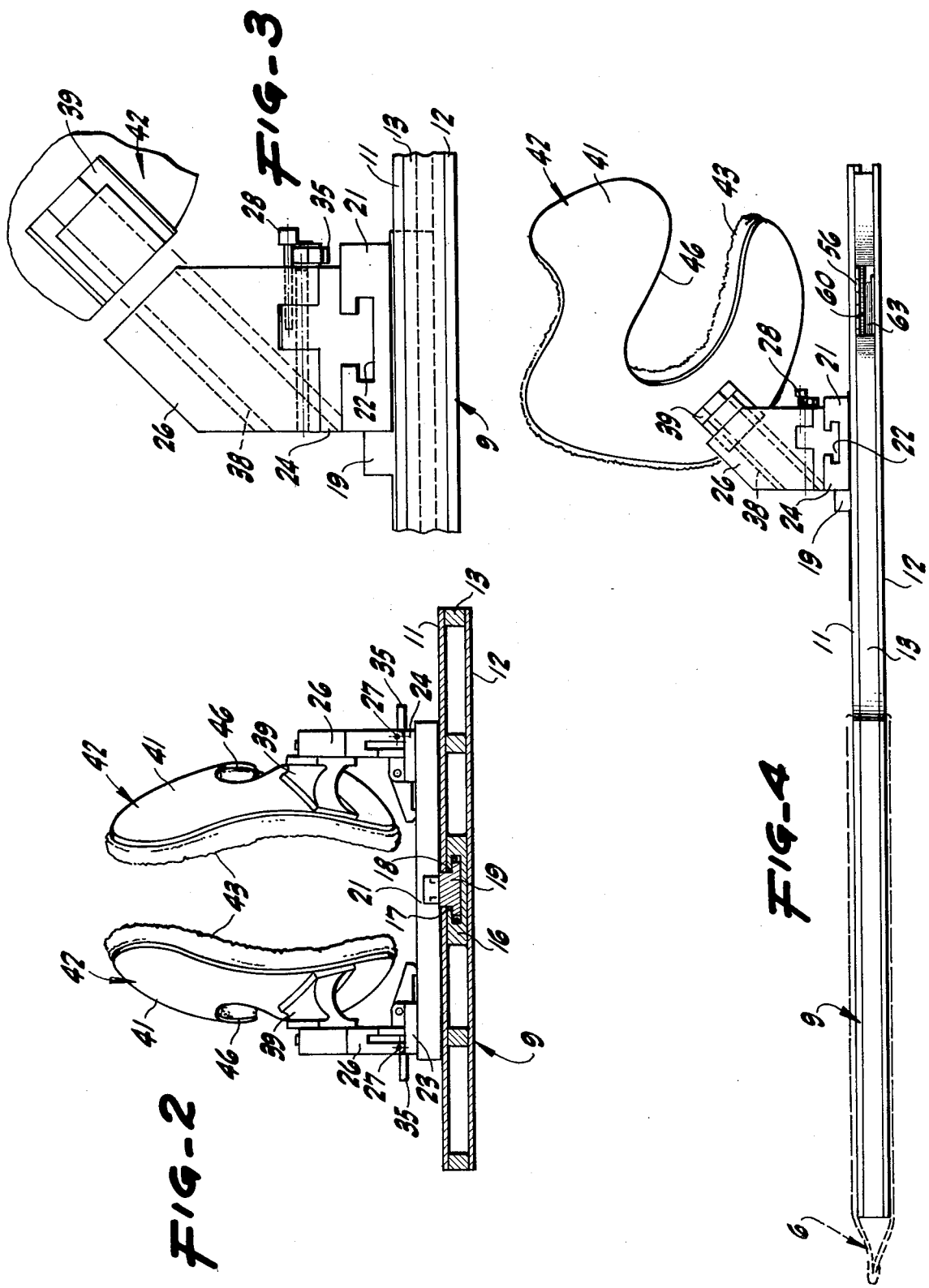

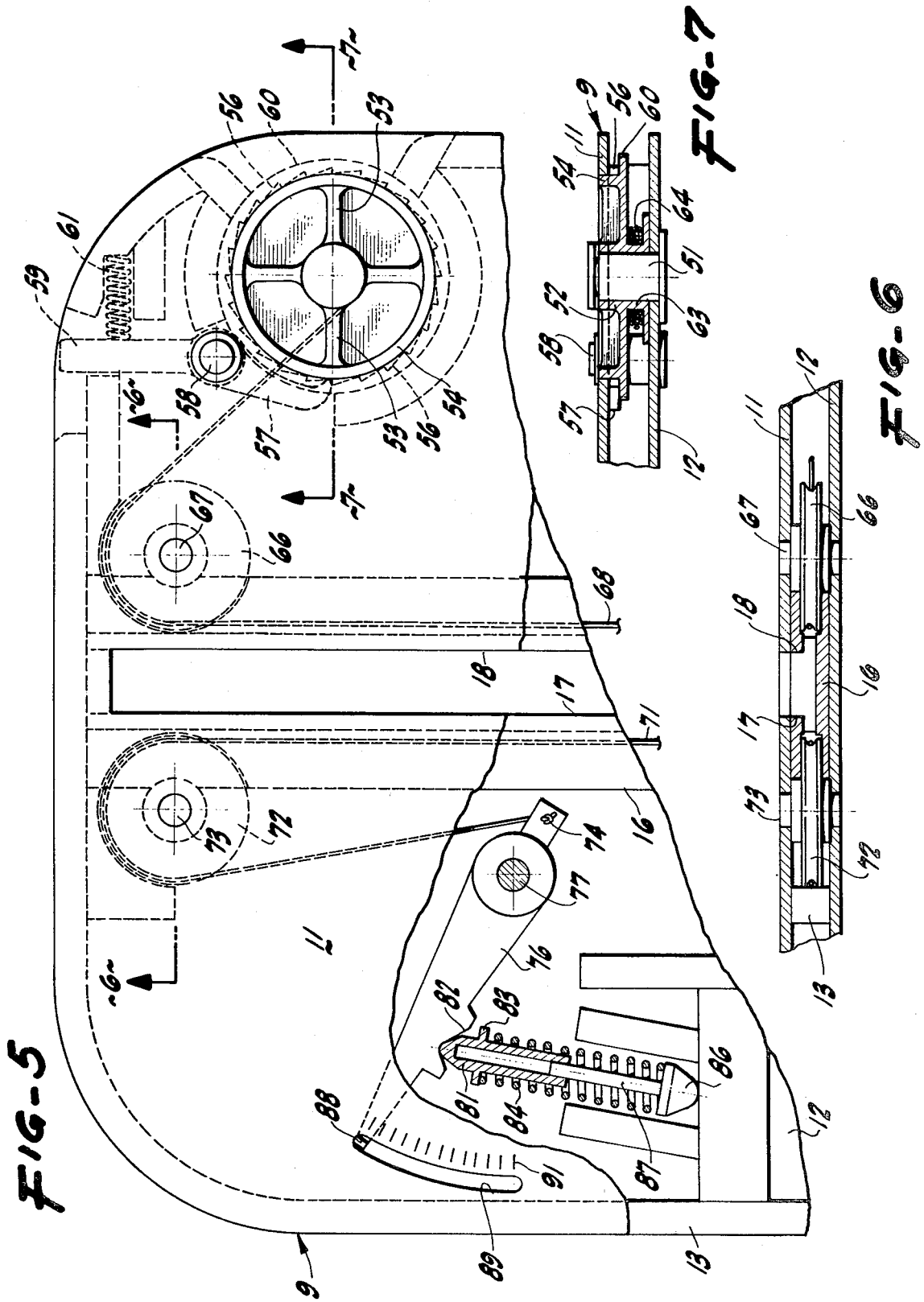

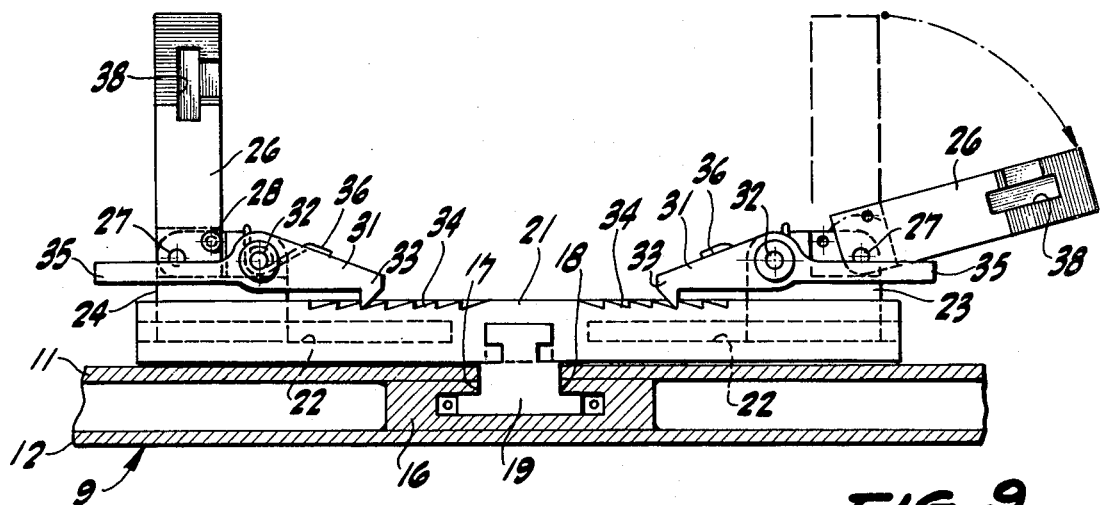
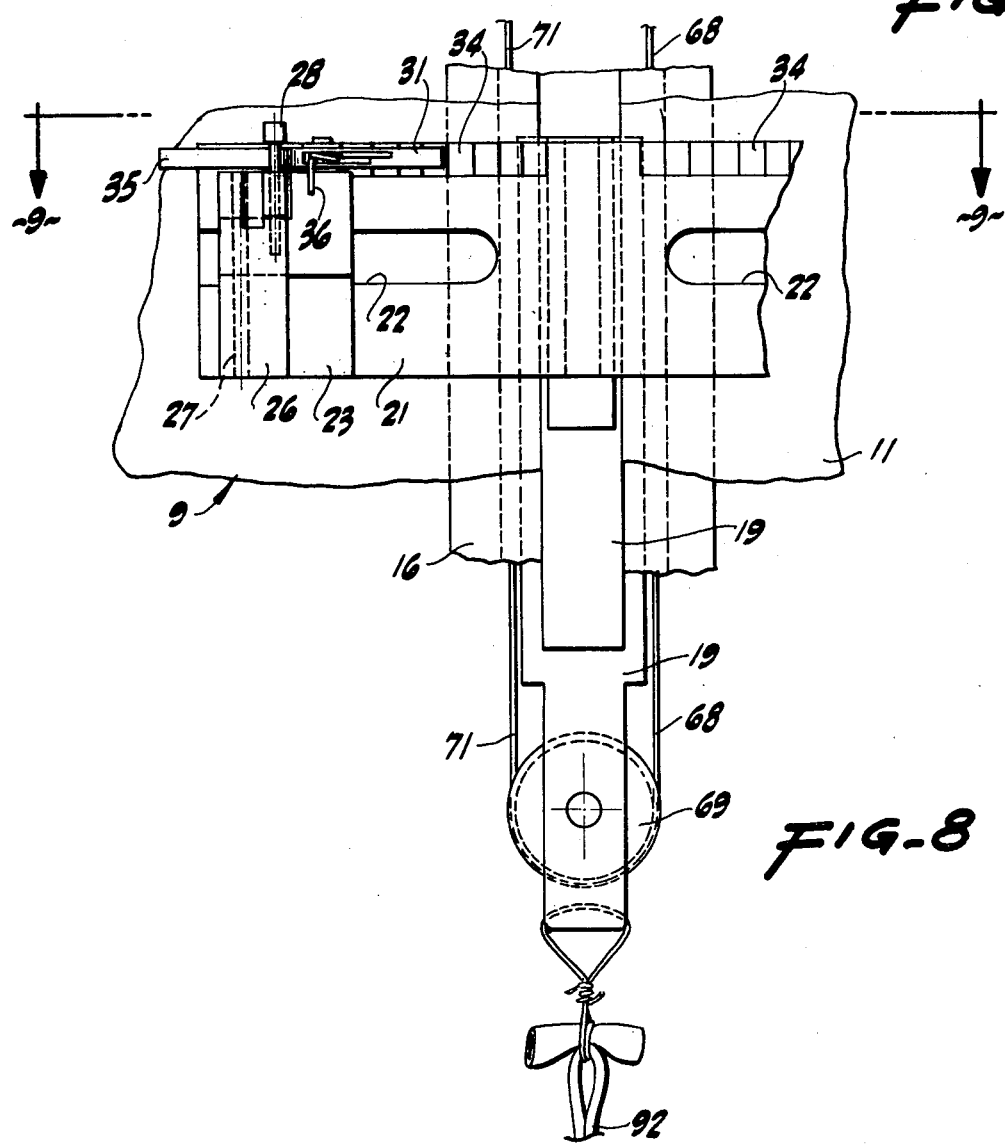

TRACTION DEVICE

BRIEF SUMMARY OF THE INVENTION

For use in aligning and holding the spinal-cranial structure of an injured patient, there is afforded a portable, buoyant base frame on which a slide is longitudinally movable by means of a manually adjusted cord tensioning a spring. On the slide are transversely positionable, facing, head-engaging cups mounted not only to be transported with the longitudinally movable slide but also for motion toward and away from each other and, in addition, relative to the slide having a component toward and away from the base frame.

PRIOR ART

Reference is made to the following United States patents:

| | | |
|---|---|---|
| 3,957,040 | May 18, 1976 | Calabrese |
| 4,015,597 | April 5, 1977 | Beaver |
| 4,141,368 | February 27, 1979 | Meyer |
| 4,194,501 | March 25, 1980 | Watt |
| 4,211,218 | July 8, 1980 | Kendrick |
| 4,220,147 | September 2, 1980 | Allen |
| 4,252,113 | February 24, 1981 | Scire |
| 4,267,830 | May 19, 1981 | Vick | and the following publications:
  Catalog 504 of Dyna Med, Carlsbad, Calif., page 5, page 6 and page 14
  The EMT Journal, June 1980, page 21
  Emergency Medical Services, July/August 1980, page 39, page 42 and page 51
  Emergency Medical Services, November/December 1980, page 121, page 165, page 170 and page 197

While these patents and publications are concerned with devices for use in assisting in maintaining the position of various body parts, they are not particularly pertinent to the present tensioning and aligning device disclosed.

BRIEF DESCRIPTION OF THE SEVERAL VIEWS OF THE DRAWINGS

FIG. 1 is a plan of a traction device constructed pursuant to the invention.

FIG. 2 is a cross-section of the device, the plane of which is indicated by the line 2—2 of FIG. 1.

FIG. 3 is a detail to an enlarged scale and in side elevation with portions broken away of some of the structure shown in FIG. 2.

FIG. 4 is a side elevation of a portion of the structure especially associated with the head-engaging cups.

FIG. 5 is a plan of a portion of the base frame, other portions being broken away, certain of the slide structure being omitted, and some of the interior construction being disclosed in a broken-away portion and illustrated in cross-section.

FIG. 6 is a detail cross-section, the plane of which is indicated by the lines 6—6 of FIG. 5.

FIG. 7 is a detail cross-section, the plane of which is indicated by the line 7—7 of FIG. 5.

FIG. 8 is a plan with portions broken away primarily showing the longitudinal slide together with the transverse slide frame and including one of the cup supports.

FIG. 9 is a cross-section, the plane of which is indicated by the line 9—9 of FIG. 8.

DETAILED DESCRIPTION

Although not necessarily limited thereto, the device of the present disclosure is especially adapted for use in accident cases wherein a victim may be lying on his back on the ground or sitting or found in a Motor Vehicle with a possible displaced or severed vertebral column. The desired immediate attention is to support, hold and locate the victim's head and spinal column with respect to each other in proper orientation and in a fashion so that the victim can be transported to a place of treatment. Sometimes the victim is involved in a water accident, for example, so that the current device is made buoyant in water for use therein as well as upon the ground. It is likewise entirely constructed of radiation translucent materials so that the patient can ultimately be subjected to x-ray or other radiation scanning or treatment without removing the present device as his support.

In the particular embodiment of the structure disclosed herein, there is provided a jacket 6 or vest which is a flexible member of a garment nature fabricated of suitable material and, for example, containing reinforcements 7 therein. The vest has appropriate fastening devices 8 so that the jacket or vest can be put around the patient's trunk or torso and fastened. The various straps 8 can conveniently go over the patient's shoulders as well as around him to position the vest snugly.

Pursuant to the invention, the jacket 6 is fastened to a suitable, subjacent base frame 9 in the nature of a "board" or actually a hollow framework of a stiff nature. Preferably, this is comprised of an upper panel 11, a lower panel 12 and appropriate intervening reinforcements 13. The linear dimensions of the board are sufficient to underlie the customary adult and have a varied width sufficient in one portion to underlie the jacket 6 to afford a rigid support thereunder and then somewhat extended so as to underlie the back and shoulders of the user as well as to underlie his head.

The base frame is provided with a longitudinally extending channel member 16 containing longitudinally extending side guides 17 and 18 to receive a slide 19 readily movable but confined to a relatively rectilinear path.

At an appropriate point, the slide 19 carries a transverse frame 21 or yoke of a configuration to define a shouldered groove 22 in which a pair of transverse slide blocks 23 and 24 are transversely movable independently of each other in separate paths. The transverse slide blocks are substantially identical, so the description of one applies equally to the other. On the slide block 23 there is afforded an upstanding slide connection 26. This is mounted for movement on the block 23 by means of a pivot pin 27 so that motion through approximately ninety degrees may be had. In the upright position of the slide connection there is an arrangement to receive a locking pin 28 going through aligned apertures in the block 23 and the upright 26 so that the upright can be maintained in a vertical location.

The transverse position of the block 23 can be arranged at any desired distance from the center line by means of a lever pawl 31 mounted by a pin 32 on the block 23. The pawl has a nose 33 (FIG. 9) designed to interfit in one direction of motion with a ratchet 34 on the transverse member 21. There is a hand lever 35 included with the ratchet mechanism so that the pawl can be lifted against the urgency of a spring 36. With this arrangement, the block 23 can be moved toward the center and, when released, away from the center of the frame 21, provided the latch lever 35 is actuated to disengage the pawl 33 from the ratchet 34. The slide block 23 is precluded from random outward movement by interengagement of the pawl and ratchet.

Designed to move within the arm 26 is a slide 38 having a tongue and groove engagement with the arm. On the slide 38 is a bracket 39 carrying a slightly flexible backing support 41 for a head-engaging cup generally designated 42 and designed to abut the side of the user's head and face. For that reason, the backing 41 is lined with a relatively soft, foamy material 43 for comfortable and ready conformation to the contour of the side of the user's head.

With this arrangement, the base frame is originally put beneath the user, either by rolling the user to one side, inserting the board and then rolling him back, or by lifting the user slightly and sliding the board beneath him. The vest 6 and its straps are positioned and fastened, and the slide 19 is approximately positioned longitudinally. The two slide blocks 23 and 24 are then brought in from a widely spaced apart transverse relationship toward a central relationship and bring in the slide connections 26 therewith.

If the connections 26 had been lowered for storage and transport, as shown at the right hand of FIG. 9, for use they are both brought into an upright position with anchor pins 28 positioned so that the arms 26 are rigidly held in a vertical orientation. When the erected arms are brought toward each other, usually in equal amounts, the pawls 33 override the ratchets 34 until the head-engaging cups 42 are brought against the opposite sides of the user's head to hold it firmly. In each of the cups 42 there is a cut-away portion 46 to accommodate the user's ears and to allow examination of the ear canals and drums. The cut-away portion 46 also affords access to the user's cranium, if needed, for subsequent in-hospital drilling and yoke attaching operations.

When the head-engaging cups have been approximately centrally positioned by transverse motion, such cups as a unit are moved longitudinally away from the vest 6 to subject the user's skull and spine to dynamic, or floating, tension in order to place them in a more nearly accurately aligned or proper relationship.

For that reason, the base frame 9 (FIGS. 5 and 7) is a support for a stud 51 carrying thereon a hub 52 having a number of radial webs 53 so that an operator by engaging his fingers with the webs can rotate the hub. The webs 53 extend between the hub and a drum rim 54 having a number of peripheral ratchet teeth 56 designed to cooperate with a ratchet 57 mounted on a pivot pin 58 on the base frame. A ratchet release lever 59 is urged in one direction by a spring 61. The drum can be unidirectionally rotated and held and also released. Additionally or alternatively, the drum rim 54 can be formed with a margin 60, preferably knurled and extending for ready accessibility into a cut-away portion of the base frame margin. Drum rotation can be effected by finger engagement with the margin 60.

Carried on the hub 52 is a cable drum 63 serving as an anchor for one end of a cable 64 or cord trained around an idle pulley 66 rotatable on a shaft 67 mounted on the base frame. The cable then extends on a longitudinal bight 68 and around a pulley 69 journalled at one end of the slide 19. From the other side of the pulley 69 a return bight 71 extends around a pulley 72 rotatable on a shaft 73 in the base frame. The cord or cable terminates in a knot 74 at one end of an indicator lever 76. A shaft 77 in the base frame mounts the lever 76 for rotation.

The lever 76 (FIG. 5) is in engagement with a spring guide 81 having a pointed end fitting in a notch 82 in the lever and also carrying a collar 83 acting as a stop for one end of a coil spring 84. The other end of the spring 84 rests against a support 86 at the end of a stem 87 telescoping with the spring guide 81. The motion of the lever 76 and the deflection of the spring is indicated by a pointer 88 at the end of the lever movable through a slot 89 in the upper face of the base frame and alongside a scale 91 to indicate the amount of deflection of the spring due to tension in the cable established by rotation of the spool 56.

When the patient's body and head have been engaged as described, the operator rotates the hub 52 by finger engagement with the webs 53 and winds the cable or cord 64 onto the drum 63. This shortens the cable and imposes a force effective to rotate the lever 76 against the urgency of the spring 84. The operator continues the spool or drum rotation or oscillation until by observation of the pointer 88 and scale 91 he has achieved the desired tension or stretching force between the patient's head and torso. When the operator releases the reel 56, there is no backward rotation in any substantial amount. The compression of the spring 84 and the desired tension between the slide 19 and the base frame is maintained. In this way, the patient is not only immobilized and supported but is maintained under sufficient tension to guard against misalignment of his head and spine. He and the traction device can then readily be transported to a hospital without serious risk of additional injury.

In the hospital, before he is released from the present structure he can be provided with appropriate traction tongs since there is room in the openings 46 for the desired skull drilling operations and the insertion of tong ends. When supplemental holding traction has been impressed upon the patient, it is feasible to release and remove the present traction device. By operating the lever 59, the tension in the cable or cord 64 is released and so that the slide 19 can readily be moved. A return tension device 92, such as a rubber band (FIGS. 1 and 8) stretched between the slide 19 and the base frame 9 assists in restoring some of the mechanism to original or relaxed condition. The locking pins 28 can be withdrawn so that the slide connections 26 can be swung out of the way. In addition, the levers 35 can be actuated to release the pawls 33 from the ratchets 34. All parts of the structure, including the vest 6, can be removed with the patient's further care being left to the customary hospitalization.

The present structure after any appropriate reconditioning can easily be available for a subsequent aqueous or ground-supported patient in need thereof.

I claim:

1. A traction device comprising a planar base frame, means defining a longitudinal guide in said base frame, a slide adapted to operate in said guide, a transverse yoke on said slide, a pair of blocks movable transversely on said yoke, connectors on said blocks, a pair of head-engaging cups, means for articulating each one of said cups for movement on a respective one of said connectors in a direction longitudinally inclined with respect to said planar base frame, and tension means for moving said cups in a predetermined longitudinal direction relative to said planar base frame.

2. A device as in claim 1 in which each of said cups is articulated with a respective one of said connectors by a sliding connection inclined with respect to said base frame and having a motion component toward and away from said base frame.

3. A device as in claim 1 in which said base frame is hollow and is buoyant in water.

4. A device as in claim 1 including means on each of said connectors forming a guide, a slide shoe on a respective one of said head-engaging cups and slidably engaging a respective one of said guides said guides and said slide shoes being disposed angularly relative to said base frame.

5. A device as in claim 1 including a manually rotatable hub, means for mounting said hub for rotation on said base frame, means for connecting said hub to move said slide, and a releasable pawl and ratchet mechanism interengaging said hub and said base frame for restraining rotation of said hub.

6. A device as in claim 5 in which said base frame has a reverse face and an obverse face and said head-engaging cups and said manually rotatable hub are accessible from said obverse face.

7. A device as in claim 1 including means engaging said base frame and engaging said slide for urging said slide toward one end of said base frame.

8. A device as in claim 1 in which said cups include cut-away portions accommodating the user's ears and affording access to the user's ear canals and drums for examination thereof.

9. A device as in claim 1 including means for causing said cups to move toward said base frame as said cups move in said predetermined longitudinal direction.

10. A device as in claim 1 including means for mounting said connectors on said blocks for pivotal movement about longitudinal axes.

* * * * *